United States Patent
Choi et al.

(10) Patent No.: US 7,375,808 B2
(45) Date of Patent: May 20, 2008

(54) METHOD AND SYSTEM FOR SENSING AND IDENTIFYING FOREIGN PARTICLES IN A GASEOUS ENVIRONMENT

(75) Inventors: Sang H. Choi, Poquoson, VA (US); Yeonjoon Park, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 11/536,120

(22) Filed: Sep. 28, 2006

(65) Prior Publication Data
US 2008/0079938 A1 Apr. 3, 2008

(51) Int. Cl.
*G01J 3/30* (2006.01)
*G01N 21/64* (2006.01)

(52) U.S. Cl. ..................................................... 356/318
(58) Field of Classification Search ................ 356/318
See application file for complete search history.

(56) References Cited

U.S. PATENT DOCUMENTS

| | | | | |
|---|---|---|---|---|
| 5,362,653 | A | * | 11/1994 | Carr et al. ................... 436/165 |
| 5,496,701 | A | | 3/1996 | Pollard-Knight |
| 5,629,213 | A | | 5/1997 | Kornuth et al. |
| 5,858,799 | A | | 1/1999 | Yee et al. |
| 5,993,634 | A | * | 11/1999 | Simpson et al. ............ 204/612 |
| 6,194,223 | B1 | | 2/2001 | Herrman et al. |
| 6,420,056 | B1 | | 7/2002 | Chondroudis et al. |
| 6,573,107 | B1 | | 6/2003 | Bowen et al. |
| 6,628,376 | B1 | | 9/2003 | Nikitin et al. |
| 6,692,974 | B2 | | 2/2004 | Perkins |
| 2004/0090630 | A1 | | 5/2004 | Tittel et al. |
| 2004/0160606 | A1 | | 8/2004 | Lakowicz et al. |
| 2005/0094150 | A1 | | 5/2005 | DePue et al. |

OTHER PUBLICATIONS

Laurent Salomon et al., "Near-Field Distribution of Optical Transmission of Periodic Subwavelength Holes in a Metal Film," Physical Review Letters, The American Physical Society, vol. 86 (No. 6), p. 1110-1113, (Feb. 5, 2001).
Y. Xie, et al., "Transmission of Light Through Periodic Arrays of Sub-Wavelength Slits in Metallic Hosts," Optics Express, vol. 14, No. 14, (Jul. 10, 2006).

* cited by examiner

*Primary Examiner*—F. L Evans
(74) *Attorney, Agent, or Firm*—Helen M. Galus

(57) ABSTRACT

An optical method and system sense and identify a foreign particle in a gaseous environment. A light source generates light. An electrically-conductive sheet has an array of holes formed through the sheet. Each hole has a diameter that is less than one quarter of the light's wavelength. The sheet is positioned relative to the light source such that the light is incident on one face of the sheet. An optical detector is positioned adjacent the sheet's opposing face and is spaced apart therefrom such that a gaseous environment is adapted to be disposed therebetween. Alterations in the light pattern detected by the optical detector indicate the presence of a foreign particle in the holes or on the sheet, while a laser induced fluorescence (LIF) signature associated with the foreign particle indicates the identity of the foreign particle.

28 Claims, 2 Drawing Sheets

METHOD AND SYSTEM FOR SENSING AND IDENTIFYING FOREIGN PARTICLES IN A GASEOUS ENVIRONMENT

ORIGIN OF THE INVENTION

The invention was made in part by employees of the United States Government and may be manufactured and used by or for the Government of the United States of America for governmental purposes without the payment of any royalties thereon or therefor.

FIELD OF THE INVENTION

This invention relates to particle detection and classification. More specifically, the invention is a method and system for sensing and identifying foreign particles in a gaseous environment.

DESCRIPTION OF THE RELATED ART

The detection and identification of airborne germs or toxic chemicals (GTC) is valuable in a variety of medical, military and commercial situations. Even low levels of GTC elements in air can be problematic or dangerous. However, low-level GTC detection/identification is not easily accomplished using current state-of-the art technology.

Most GTC detection systems are laboratory scale arrangements of bulky and complex equipment that use some type of "wet" processing to capture and hold GTC elements during detection scrutiny. The laboratory scale set-ups are not easily adapted to "real world" situations where air samples must be captured and then introduced into the laboratory set-up without contaminating the air sample. Furthermore, since current GTC detection systems consume the sample, the difficult sample collection process may need to be repeated multiple times.

SUMMARY OF THE INVENTION

Accordingly it is an object of the present invention to provide a method and system for sensing and identifying foreign particles (e.g., germs or toxic chemicals) in a gaseous environment.

Another object of the present invention is to provide a method and system for sensing and identifying airborne foreign particles.

Still another object of the present invention is to provide a method and system of airborne foreign particle detection/identification that can be adapted for field use.

Other objects and advantages of the present invention will become more obvious hereinafter in the specification and drawings.

In accordance with at least one embodiment of the present invention, an optical method and system are provided for use in sensing and identifying a foreign particle in a gaseous environment. A light source generates light having a known wavelength. An electrically-conductive sheet has first and second faces opposing one another with an array of holes formed through the sheet and extending between the first and second faces. Each hole has a diameter that is less than one quarter of the light's known wavelength. The sheet is positioned relative to the light source such that the light is incident on the sheet's first face. An optical detector is positioned adjacent the sheet's second face and is spaced apart therefrom such that a gaseous environment is adapted to be disposed therebetween. The optical detector is used to monitor a light pattern at the sheet's second face. Alterations in the light pattern detected by the optical detector indicate the presence of a foreign particle in the holes or on or very near to the sheet's second face. A laser induced fluorescence (LIF) signature associated with the foreign particle is indicative of the identity of the foreign particle.

DETAILED DESCRIPTION OF THE INVENTION

Figure 1:
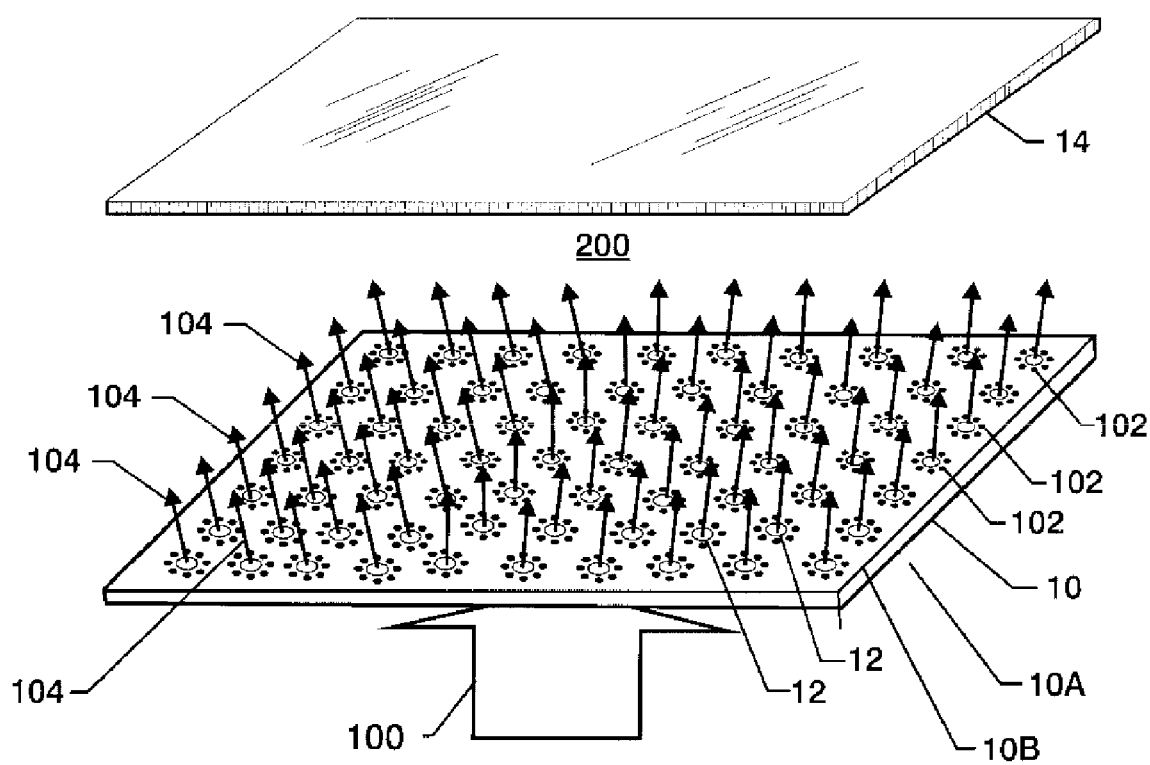
FIG. 1 is a schematic view illustrating the concepts used in foreign particle sensing and identifying in accordance with the present invention.

Prior to describing the methods and system of the present invention, the optical principles utilized by the present invention will be explained. In principle, holes in an opaque metallic sheet or film that are smaller than the wavelength of a particular light wave do not permit photon transmission therethrough. Holes in this size range are known as "quantum apertures" (QA). However, it has recently been discovered that holes in a metallic thin-film that are 10 times smaller than a particular wavelength still allow transmission of a light wave. See Ebbesen et al., "Extraordinary Optical Transmission Through Sub-wavelength Hole Arrays," Nature, Vol. 391, p. 667-669, February 1998.

The most well-accepted theory as to what happens to light impinging on a metal thin-film having a QA array is that the light is making its way through the holes in the form (or with the assistance) of a "surface plasmon polariton" (SPP). See Salomon et al., "Near-field Distribution of Optical Transmission of Periodic Subwavelength Holes in a Metal Film," Phys. Rev. Lett., Vol. 86, p. 1110-1113, 2001; and Xie et al., "Transmission of Light Through Periodic Arrays of Sub-wavelength Slits in Metallic Hosts," Optics Express, Vol 14 (No. 14), p. 6400-6413, 2006. Briefly, "surface plasmon" (SP) is the term given to describe non-radiating electromagnetic (EM) disturbances arising from the collective movements of electrons at conductor-insulator interfaces. The plasmons and the photons of light form a composite object known as a "surface plasmon polariton" where a "polariton" is a combination of photons and another type of object. Combining the SPP with a regular arrangement of holes results in a "polaritonic crystal." The cooperative effect of many holes in the polaritonic crystal leads to the creation of an EM field that is most intense close to or at the location of the holes.

Another explanation of this optical phenomena is that the light gets through the holes in the form of an SP "molecule" (SPM) consisting of two polaritons, one on each side of the metal film. See Martin-Moreno et al., "Theory of Extraordinary Optical Transmission Through Subwavelength Hole Arrays", Phys. Rev. Lett., 86, 1114, 2001. Martin-Moreno et al. suggest that the two polaritons interact with one another with exponentially decaying EM fields thereby forming molecular levels in very much the same way that atomic electron wave functions interact to form molecular levels in a diatomic molecule.

Still a third explanation of these optical phenomena is possible. More specifically, when light is either blocked by a total reflection beyond a Brewster angle or coupled with surface plasmon to develop a polariton wave that may be directed and confined in a tiny hole, the decaying near-field EM waves through a tiny hole make a dominant interaction with the object behind the reflecting plane and hole. In other words, the surface plasmon or collective behavior of electrons grouped on a metallic film surface is disrupted by the presence of the object. Accordingly, the emission spectra conveyed through an object-disturbed polariton wave of surface plasmon is shifted due to the energy loss of the polariton wave.

Any one of these three explanations supports the theory that in the case of a QA array in a metal film, the EM field is developed at the holes or interacts with the EM field at the other side of metal film. This near-field optical interaction and the collective (or ordered) motion of electrons (i.e., the SPP) through the wall surfaces of the QA array while or after coupling with photons of light are important factors for these phenomena. (Such an ordered motion of electrons establishes electron wave functions through the holes with a variety of user-adjustable parameters being able to dictate the behavior of the ordered electrons. Such user-adjustable parameters include the diameter of the holes, hole-depth, array period, thin-film material electrical properties, surface topology of the thin-film, uniformity of the holes, and thin-film substrates.) If the ordered state of electrons corresponding to the photons of impinging light waves is altered by the presence of a disruptive object, the transmitted light wave through the QA array can be spectrally shifted, switched off/on, or dimmed depending on the size and/or position of the object.

Referring now to FIG. 1, the above-described optical principles are applied in the sensing and identifying of foreign particles in a gaseous medium. For example, the foreign particles could be germs or toxic chemicals (GTC) and the gaseous medium could be air. However, it is to be understood that the nature of the foreign particles or gaseous medium are not limitations of the present invention.

As shown, in FIG. 1, an electrically-conductive sheet (e.g., a metallic thin-film) 10 is positioned such that laser light or white light (indicated by arrow 100) is incident on a surface 10A of sheet 10. As will be explained further below, laser light is preferred when using the present invention to sense and identify foreign particles. Sheet 10 has a regularly shaped pattern or array of holes 12 formed therethrough. That is, holes 12 extend from surface 10A of sheet 10 all the way through to opposing surface 10B of sheet 10. While the hole pattern and shape may vary, typically, holes 12 are circular in cross-section, identical in size, and regularly arranged on an x-y plane with a spacing between the holes greater than 0.5 the diameter of the holes. In the present invention, the diameter of each hole 12 must be less than one quarter of the wavelength of light 100. By controlling hole size in this way, transmission of light 100 through sheet 10 (via holes 12) is governed by the above-described SPP. The SPP is illustrated by the circular array of electrons 102 around each hole 12 and the light transmission pattern indicated by arrows 104. In FIG. 1, it is assumed that no foreign particles are present in a gaseous medium 200 adjacent surface 10B of sheet 10. Accordingly, light transmission through sheet 10 is said to be caused by an undisturbed SPP where the light wave transmitted through the array of holes 12 maintains the same wavelength at the exit plane (i.e., surface 10B) without spectral or diffraction shift. Since holes 12 are provided in a regularly-shaped pattern or array, the resulting undisturbed SPP generated at surface 10B is regularly-shaped. Detection and monitoring of the undisturbed SPP pattern can be accomplished in a macroscopic sense by monitoring light pattern 104 with an optical detection system 14 such as a charge coupled device (CCD) as will be explained later below.

The macroscopically detected/monitored undisturbed SPP pattern serves as a benchmark comparison during the sensing and identifying of foreign particles in accordance with the present invention. More specifically, when a foreign particle (not shown) that is larger than holes 12 lands on surface 10B (or is suspended very close thereto), the generated SPP pattern is disturbed/altered in some way, e.g., partially blacked out, dimmed, or spectrally shifted. Thus, a detected disturbance in the SPP pattern indicates the presence of a foreign particle. A disturbance or alteration in the generated SPP pattern can also occur even when the foreign particles are smaller than the diameter of holes 12 such that they become trapped within holes 12. In such a case, the resulting light wave disturbance is analogous to an electromagnetic waveguide that has a foreign object within the waveguide.

Figure 2:
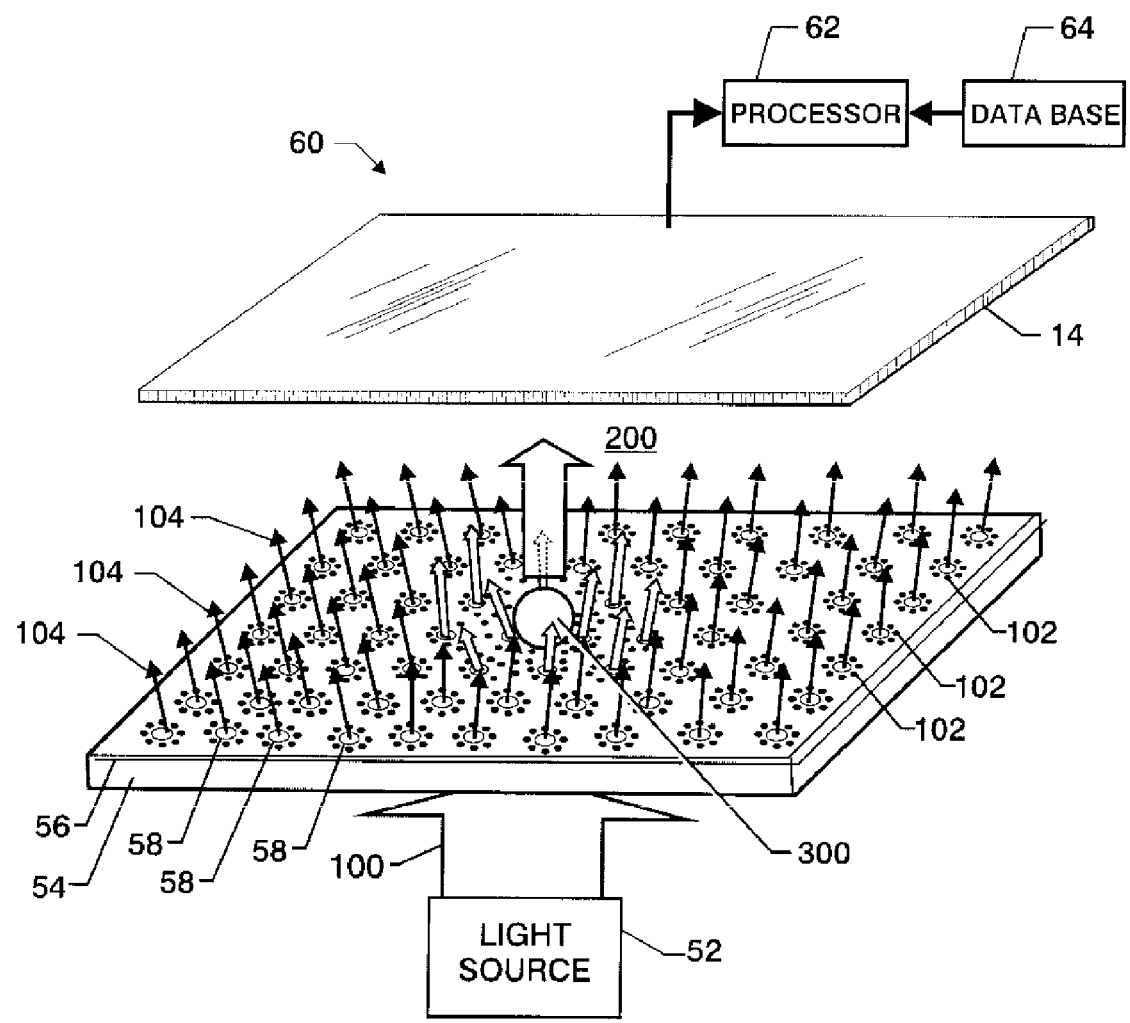
FIG. 2 is a schematic view of an optical system for sensing and identifying a foreign particle in a gaseous environment in accordance with an embodiment of the present invention.

Referring now to FIG. 2, the above-described principles are incorporated into an optical system 50 for identifying a foreign particle in a gaseous environment. Optical system 50 includes:
    a light source 52 for generating laser or white light 100,
    a light transmissive (i.e., at least transmissive with respect to the wavelength of light 100) substrate 54,
    an electrically-conductive metallic thin-film 56 having an array of holes 58 formed therethrough,
    an optical detector 60 spaced apart from thin-film 56,
    a processor 62 coupled to optical detector 60 to receive the output therefrom, and
    a database 64 coupled to or integrated with processor 62.

Light source 52 is any source capable of producing laser or white light 100 that will pass through substrate 54 before being incident on thin-film 56. White light can be used when only the detection of foreign particles is required whereas laser light is used when the foreign particles must be detected and identified as will be explained further below.

Thin-film 56 is typically first developed on an optically transparent substrate 54 with the array of holes 58 and any desired thin-film surface topology being subsequently formed using fabrication processing well known in the art. Substrate 54 provides structural support for thin-film 56 while being optically transmissive to at least light 100. A suitable and readily-available material for substrate 54 is quartz glass as it has a broad spectrum of light transmission. Thin-film 56 and holes 58 must satisfy the requirements set forth herein above, i.e., holes 58 have diameters that are less than one quarter the wavelength of light 100.

Optical detector 60 is any device/system capable of detecting the emission associated with the SPP pattern that will be generated by light 100 as it impinges on thin-film 56 having an array of holes 58. For example, optical detector 60 can be a CCD array covering the area defined by the array of holes 58. The resolution of optical detector 60 will depend on the size of a potential foreign particle of interest.

A foreign particle of interest 300 within air 200 will be detected by system 50 when landing on thin-film 56, i.e., particle 300 is at least larger than one of holes 58. As a result of the presence of particle 300 on thin-film 56, electrons 102 and the resulting transmitted light pattern 104 (i.e., indicative of the SPP emission on a macroscopic level) are disturbed in the region around particle 300 as illustrated. As mentioned above, disturbances in the SPP pattern can also be caused by foreign particles that are small enough to fit within holes 58 such that they are trapped therein. Note that if the size of the foreign particle is very small relative to the hole diameter, the disruptive effect is diminished. Additionally, as also mentioned above, foreign particles suspended very close to the thin-film 56 can also influence, or disturb the SPP pattern. In all of these cases, detection of foreign particle 300 can be accomplished by monitoring light pattern 104 using optical detector 60/processor 62. More specifically, processor 62 compares the monitored light pattern 104 with the undisturbed benchmark light pattern 104 (FIG. 1) in order to detect the presence of particle 300.

When light 100 is laser light, the actual light transmitted through thin-film 56 can also induce fluorescence from particle 300 as the photon energy absorbed by particle 300 causes a level transition of quantum structure. This level transition causes a fluorescent transmission (i.e., laser induced fluorescence or "LIF") from particle 300. As is known in the art, the LIF of a material is a spectral signature that can identify the material. Accordingly, database 64 can be used to store a variety of spectroscopy measurement results for types of foreign particles of interest. Since the LIF signature can be used to identify particle 300, in at least one embodiment, optical detector 60 will include the means (e.g., a spectrometer) for measuring the LIF signature associated with particle 300.

The advantages of the present invention are numerous. Airborne foreign particle (e.g., GTC) detection and identification can be accomplished quickly and easily in the field. The issues associated with sample collection and sample destruction are virtually eliminated. The present invention can be readily adapted for sensitivity to a variety of types of foreign particles by providing different quantum aperture arrays, where typical parameters that can be adjusted include diameter of the holes, hole depth, spacing between the holes, surface topology of the thin-film (e.g., especially around the holes), thin-film electrical properties, and the substrate material supporting the thin-film.

Although the invention has been described relative to a specific embodiment thereof, there are numerous variations and modifications that will be readily apparent to those skilled in the art in light of the above teachings. For example, it may be desirable to make optical detector 60 movable with respect to thin-film 56 so that detector 60 does not block or otherwise prevent foreign particles from landing on thin-film 56. That is, optical detector 60 could be coupled to some sort of actuator that positioned detector 60 over thin-film 56 at measurement times. Additional thin-films 56 could also be provided so that there would always be at least one thin-film 56 exposed to the gaseous environment even while optical detector 60 was making measurements. Still further, a single thin-film could have multiple arrays of holes formed therethrough with the thin-film being movable so that a particular array of holes could be aligned with an optical detector. Each array of holes could be identically configured or uniquely configured to suit a particular application. It is therefore to be understood that, within the scope of the appended claims, the invention may be practiced other than as specifically described.

What is claimed as new and desired to be secured by Letters Patent of the United States is:

1. An optical system for use in sensing and identifying a foreign particle in a gaseous environment, comprising:
   a light source for generating light having a known wavelength;
   an electrically-conductive opaque sheet having first and second faces opposing one another with an array of holes formed through said sheet and extending between said first and second faces, each of said holes having a diameter that is less than one quarter of said known wavelength, said sheet positioned relative to said light source such that said light is incident on said first face; and
   optical detection means positioned adjacent said second face and spaced apart therefrom such that a gaseous environment is adapted to be disposed therebetween, said optical detection means detecting a light pattern at said second face when said light is incident on said first face, wherein alterations in said light pattern are indicative of the presence of a foreign particle between said first face and said optical detection means.

2. An optical system as in claim 1 wherein said light source comprises a laser, and wherein a laser induced fluorescence (LIF) signature associated with the foreign particle is indicative of the identity of the foreign particle.

3. An optical system as in claim 1 further comprising a light transmissive substrate coupled to said sheet.

4. An optical system as in claim 3 wherein said light transmissive substrate comprises quartz glass.

5. An optical system as in claim 2 wherein said optical detection means comprises:
   a charge coupled device (CCD) array for detecting said light pattern; and
   a spectrometer for measuring said LIF signature.

6. An optical system as in claim 1 wherein said sheet defines a plane and said light is incident on said first face at a substantially perpendicular angle to the plane of said sheet.

7. An optical system as in claim 1 wherein:
   said holes are identically-sized; and
   said sheet has a substantially uniform thickness and defines a plane.

8. An optical system for sensing and identifying a foreign particle in a gaseous environment, comprising:
   a light source for generating light having a known wavelength;
   an electrically-conductive opaque sheet which has a substantially uniform thickness having first and second faces opposing one another with an array of holes formed through said sheet and extending between said first and second faces, each of said holes having a diameter that is less than one quarter of said known wavelength, said sheet defining a plane and positioned relative to said light source such that said light is incident on said first face at a substantially perpendicular angle to the plane of said sheet;
   optical detection means positioned adjacent said second face and spaced apart therefrom such that a gaseous environment is adapted to be disposed therebetween, said optical detection means detecting a light pattern at said second face when said light is incident on said first face, wherein alterations in said light pattern are indicative of the presence of a foreign particle between said first face and said optical detection means.

9. An optical system as in claim 8 wherein:
   said light source comprises a laser,
   said optical detection means further measures a laser induced fluorescence (LIF) signature associated with the foreign particle; and
   said optical system further comprises processing means coupled to said optical detection means for identifying the foreign particle using said LIF signature.

10. An optical system as in claim 8 further comprising a light transmissive substrate coupled to said sheet.

11. An optical system as in claim 10 wherein said light transmissive substrate comprises quartz glass.

12. An optical system as in claim 9 wherein said optical detection means comprises:

a charge coupled device (CCD) array for detecting said light pattern; and a spectrometer for measuring said LIF signature.

13. An optical system as in claim 9 wherein said processing means includes a database of known LIF signatures with which said LIF signature of the foreign particle is compared.

14. An optical system according to claim 8 wherein said holes are identically-sized.

15. An optical system for sensing and identifying a foreign particle in a gaseous environment comprising:

a laser for generating laser light having a known wavelength;

a substrate that is transmissive with respect to said laser light;

a metallic thin-film having first and second faces opposing one another with said first face being coupled to said substrate, said metallic thin-film having an array of identically-sized holes formed therethrough and extending between said first and second faces thereof, each of said holes having a diameter that is less than one quarter of said known wavelength, said metallic thin-film positioned relative to said laser such that said laser light is incident on said first face after passing through said substrate;

optical detection means positioned adjacent said second face and spaced apart therefrom such that a gaseous environment is adapted to be disposed therebetween, said optical detection means detecting a light pattern at said second face when said light is incident on said first face, wherein alterations in said light pattern are indicative of the presence of a foreign particle between said first face and said optical detection means, said optical detection means further measuring a laser induced fluorescence (LIF) signature associated with the foreign particle; and processing means coupled to said optical detection means for identifying the foreign particle using said LIF signature.

16. An optical system as in claim 15 wherein said substrate comprises quartz glass.

17. An optical system as in claim 15 wherein said optical detection means comprises:

a charge coupled device (CCD) array for detecting said light pattern; and a spectrometer for measuring said LIF signature.

18. An optical system as in claim 15 wherein said processing means includes a database of known LIF signatures with which said LIF signature of the foreign particle is compared.

19. An optical system as in claim 15 wherein said metallic thin-film defines a plane and said laser light is incident on said first face at a substantially perpendicular angle to the plane of said sheet.

20. An optical system as in claim 15 wherein said metallic thin-film has a substantially uniform thickness which defines a plane.

21. A method of sensing and identifying a foreign particle in a gaseous environment, comprising:

generating light having a known wavelength;

providing an electrically-conductive opaque sheet having first and second faces opposing one another with an array of holes formed through said sheet and extending between said first and second faces, each of said holes having a diameter that is less than one quarter of said known wavelength, said sheet positioned such that said light is incident on said first face;

detecting a light pattern at said second face when said light is incident on said first face, wherein alterations in said light pattern are indicative of the presence of a foreign particle between said first face and said optical detection means.

22. A method according to claim 21 wherein said light is laser light, and said method further comprises detecting a laser induced fluorescence (LIF) signature associated with the foreign particle wherein said LIF signature is indicative of the identity of the foreign particle.

23. A method according to claim 21 wherein said sheet defines a plane; and further comprising the step of positioning said sheet so that the light is incident on said first face at a substantially perpendicular angle to the plane of said sheet.

24. A method according to claim 21 wherein:

said holes are identically-sized; and said sheet has a substantially uniform thickness defining a plane.

25. A method of sensing and identifying a foreign particle in a gaseous environment, comprising:

providing a metallic thin-film having a quantum aperture array formed therethrough;

generating light having a known wavelength;

positioning the thin-film in the light such that a surface plasmon polariton (SPP) is generated at a face of the thin-film;

monitoring an emission pattern of the SPP wherein a disturbance in the emission pattern is indicative of the presence of a foreign particle.

26. A method according to claim 25 wherein said light is laser light, and said method further comprises measuring a laser induced fluorescence (LIF) signature associated with the foreign particle wherein said LIF signature is indicative of the identity of the foreign particle.

27. A method according to claim 25 wherein:

said thin-film defines a plane; and said positioning step comprises positioning said thin-film so that the light is incident on said metallic thin-film at a substantially perpendicular angle to the plane.

28. A method according to claim 25 wherein:

said apertures are identically-sized; and said thin-film has a substantially uniform thickness which defines a plane.

\* \* \* \* \*